United States Patent
Chen et al.

Patent Number: 5,688,950
Date of Patent: Nov. 18, 1997

[54] TRICYCLIC AMINOALKYLCARBOXAMIDES; NOVEL DOPAMINE D₃ RECEPTOR SUBTYPE SPECIFIC LIGANDS

[75] Inventors: Xi Chen, New Haven; Jun Yuan, Clinton; Andrew Thurkauf, Danbury, all of Conn.

[73] Assignee: Neurogen Corporation, Branford, Conn.

[21] Appl. No.: 636,662

[22] Filed: Apr. 23, 1996

[51] Int. Cl.⁶ .......... C07D 221/06; C07D 241/40; C07D 241/36
[52] U.S. Cl. .......... 544/354; 544/355; 546/101
[58] Field of Search .......... 546/101; 544/354, 544/355

[56] References Cited

U.S. PATENT DOCUMENTS 5,395,835  3/1995  Glase et al. .............. 514/254

FOREIGN PATENT DOCUMENTS 206 225 A2  12/1996  European Pat. Off.
WO 95/11903  5/1995  WIPO

OTHER PUBLICATIONS

Murray et al., (1995), "A Novel Series of Arylpiperazines with High Affinity and Selectivity for the Dopamine D₃ Receptor," *Biorg. Med. Chem. Let.*, vol. 5, No. 3, pp. 219–222.

*Primary Examiner*—Mukund J. Shah
*Assistant Examiner*—Deepak R. Rao
*Attorney, Agent, or Firm*—McDonnell Boehnen Hulbert & Berghoff

[57] ABSTRACT

Disclosed are compounds of the formula:

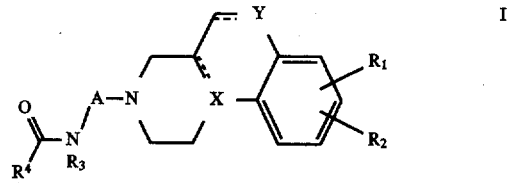

or the pharmaceutically acceptable acid addition salts thereof wherein:

$R_1$–$R_4$ represent organic or inorganic groups;

A represents an alkylene group of 2 to 6 carbon atoms optionally substituted with one or more alkyl groups having from 1 to 4 carbon atoms;

Y represents methylene, oxygen, sulfur, or NH; and

X is either N, C or CH, which compounds are useful in the treatment of affective disorders such as schizophrenia, depression, Alzheimer's disease, movement disorders such as Parkinsonism and dystonia, and other disorders which respond to dopaminergic blockade such as substance abuse and obsessive compulsive disorders. Further, compounds of this invention may be useful in treating the extrapyramidal side effects associated with the use of conventional neuroleptic agents.

23 Claims, No Drawings

TRICYCLIC AMINOALKYLCARBOXAMIDES; NOVEL DOPAMINE $D_3$ RECEPTOR SUBTYPE SPECIFIC LIGANDS

BACKGROUND OF THE INVENTION

1. Field of the Invention

This invention relates to tricyclic aminoalkylcarboxamide derivatives which selectively bind to brain dopamine receptor subtypes. It also relates to pharmaceutical compositions comprising such compounds. It further relates to the use of such compounds in the treatment or prevention of various neuropsychochological disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_3$ receptor subtype has recently been identified (Sokoloff et at., Nature, 347, 146 (1990)). Its unique localization in limbic brain areas and its differential recognition of various antipsychotics suggest that the $D_3$ receptor plays a role in the etiology of schizophrenia. Selective $D_3$ antagonists thus are expected to be effective antipsychotics free from the neurological side effects displayed by conventional neuroleptics.

U.S. Pat. No. 5,395,835 discloses N-aminoalkyl-2-napthalamides described to have affinity at dopamine $D_3$ receptors.

Murray et at., Bioorg. Med. Chem. Let. 5:219 (1995), describe 4-carboxamidobiphenyls said to have affinity at dopamine $D_3$ receptors.

International Patent Application WO 9511903 discloses tricylic diazaphenanthrene carboxamides having affinity for 5-HT$_{1A}$ receptors.

European Patent Application EP 206225 A2 discloses aryl alkyl azatricyclic compounds.

SUMMARY OF THE INVENTION

This invention provides novel compounds of Formula I which interact with dopamine receptor subtypes. Thus, the invention provides compounds of general Formula I useful in the treatment and/or prevention of various neuropsychological disorders. The invention also provides pharmaceutical compositions comprising compounds of Formula I.

Since dopamine $D_3$ receptors are concentrated in the limbic system (Taubes, Science, 265:1034 (1994)) which controls cognition and emotion, compounds which interact with these receptors also have utility in the treatment of cognitive disorders. Such disorders include cognitive deficits which are a significant component of the negative symptoms (social withdrawal and unresponsiveness) of schizophrenia. Other disorders involving memory impairment or attention deficit disorders can also be treated with the compounds of this invention which interact specifically with the dopamine $D_3$ receptor subtype.

The invention thus encompasses the use of such compounds and compositions in the treatment of affective disorders such as schizophrenia, depression, Alzheimer's disease and certain movement disorders such as Parkinsonism and dystonia. Compounds of this invention are also useful in treating the extrapyramidal side effects associated with the use of conventional neuroleptic agents. Further, the compounds of the present invention are useful for the treatment of other disorders which respond to dopaminergic blockade such as substance abuse and obsessive compulsive disorder.

Accordingly, a broad embodiment of the invention is directed to a compound of Formula I:

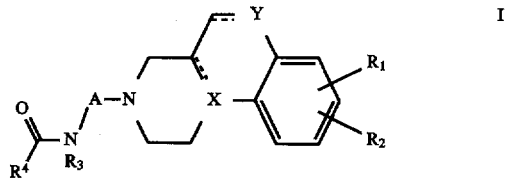

or the pharmaceutically acceptable acid addition salts thereof wherein:

R1, and $R_2$ are the same or different and represent hydrogen, $C_1-C_6$ alkyl, halogen, hydroxy, amino, cyano, nitro, trifluoromethyl, trifluoromethoxy, $C_1-C_6$ alkoxy, —O$_2$CR', —NHCOR', —COR', —SO$_n$R', where R' is $C_1-C_6$ alkyl and wherein m is 0, 1 or 2; or $R_1$ and $R_2$ independently represent —CONR'R", or —NR'R" where R' and R" independently represent hydrogen or $C_1-C_6$ alkyl;

$R_3$ is hydrogen or lower alkyl;

A represents an alkylene group of 2 to 6 carbon atoms optionally substituted with one or more alkyl groups having from 1 to 4 carbon atoms;

Y represents methylene, oxygen, sulfur, or NH;

X is either N, C, or CH; and $R_4$ is biphenyl, naphthyl, 1 or 2 anthracenyl, 1 or 2 biphenylenyl, dibenzofuranyl, dibenzothiophenenyl, fluorenyl, fluorenonyl, anthroquinonyl, 2-quinoxalinyl or azabiphenyl, each of which is optionally substituted independently by up to three groups selected from halogen, $C_1-C_6$ alkyl, $C_1-C_4$ alkoxy, alkylthio, hydroxy, amino, monoalkylamino, dialkylamino, cyano, nitro, trifluoromethyl or trifluoromethoxy.

Thus, the invention provides compounds of Formula I useful in the treatment and/or prevention of neuropsychochological disorders including, but not limited to, schizophrenia, Alzheimer's disease, mania, dementia, depression, anxiety, compulsive behavior, substance abuse, memory impairment, cognitive deficits, Parkinson-like motor disorders such as dystonia, and motion disorders and extrapyramidal side effects related to the use of neuroleptic agents.

DETAILED DESCRIPTION OF THE INVENTION

Compounds of the present invention demonstrate high affinity and selectivity in binding to the $D_3$ receptor subtype. They are therefore useful in treatment of schizophrenia, psychotic depression and mania. Other dopamine-mediated diseases such as Parkinsonism and tardive dyskinesias can also be treated directly or indirectly by modulation of $D_3$ receptors.

Furthermore, compounds of this invention can be used in treatment of memory-impairment or Alzheimer's disease by modulation of $D_3$ receptors which selectively exist in limbic area known to control emotion and cognitive functions. The compounds of the present invention are also useful for the treatment of other disorders which respond to dopaminergic blockade such as substance abuse (Caine and Koob, Science, 260:1814 (1993)) and obsessive compulsive disorder (Goodman et at., Clin. Psychopharmacol., 7:35 (1992). The compounds of the invention interact with dopamine receptor subtypes resulting in the pharmacological activity of these compounds.

In addition to compounds of general Formula I described above, the invention encompasses compounds of Formula II:

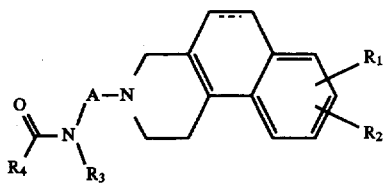

wherein $R_1$–$R_4$, and A are as defined above for Formula I.

Preferred compounds of formula II include those where $R_3$ is hydrogen, methyl or ethyl, and A is alkylene of 3–5 carbon atoms. Particularly preferred compounds of Formula II are those where $R_3$ is hydrogen, and A is butylene.

The invention also provides compounds of Formula IIA:

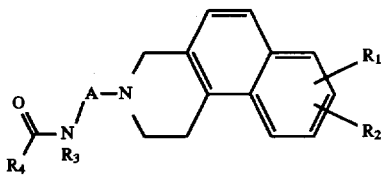

wherein $R_1$–$R_4$, and A are as defined above for Formula I.

Preferred compounds of Formula IIA include those where $R_3$ is hydrogen, methyl or ethyl, and A is alkylene of 3–5 carbon atoms. Particularly preferred compounds of Formula IIA are those where $R_3$ is hydrogen, and A is butylene.

The invention also provides compounds of Formula IIB:

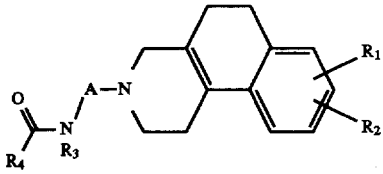

wherein $R_1$–$R_4$, and A are as defined above for Formula I.

Preferred compounds of Formula IIB include those where $R_3$ is hydrogen, methyl or ethyl, and A is alkylene of 3–5 carbon atoms. Particularly preferred compounds of Formula IIB are those where $R_3$ is hydrogen, and A is butylene.

The invention also provides compounds of Formula III:

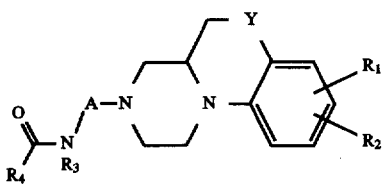

wherein $R_1$–$R_4$, A and Y are as defined above for Formula I.

Preferred compounds of Formula III include those where $R_3$ is hydrogen, methyl or ethyl, and A is alkylene of 3–5 carbon atoms. More preferred compounds of Formula III are those where Y is oxygen or sulfur, $R_3$ is hydrogen, methyl or ethyl, and A is alkylene of 3–5 carbon atoms. Particularly preferred compounds of Formula III are those where Y is oxygen or sulfur, $R_3$ is hydrogen, and A is butylene.

In addition, the invention encompasses compounds of Formula IIIA, i.e, compounds of Formula III where Y is methylene.

In addition, the invention encompasses compounds of Formula IIIB, i.e, compounds of Formula III where Y is oxygen.

In addition, the invention encompasses compounds of Formula IIIC, i.e, compounds of Formula III where Y is sulfur.

In addition, the invention encompasses compounds of Formula IIID, i.e, compounds of Formula III where Y is NH.

Preferred compounds of the invention include $R_4$ groups selected from the following:

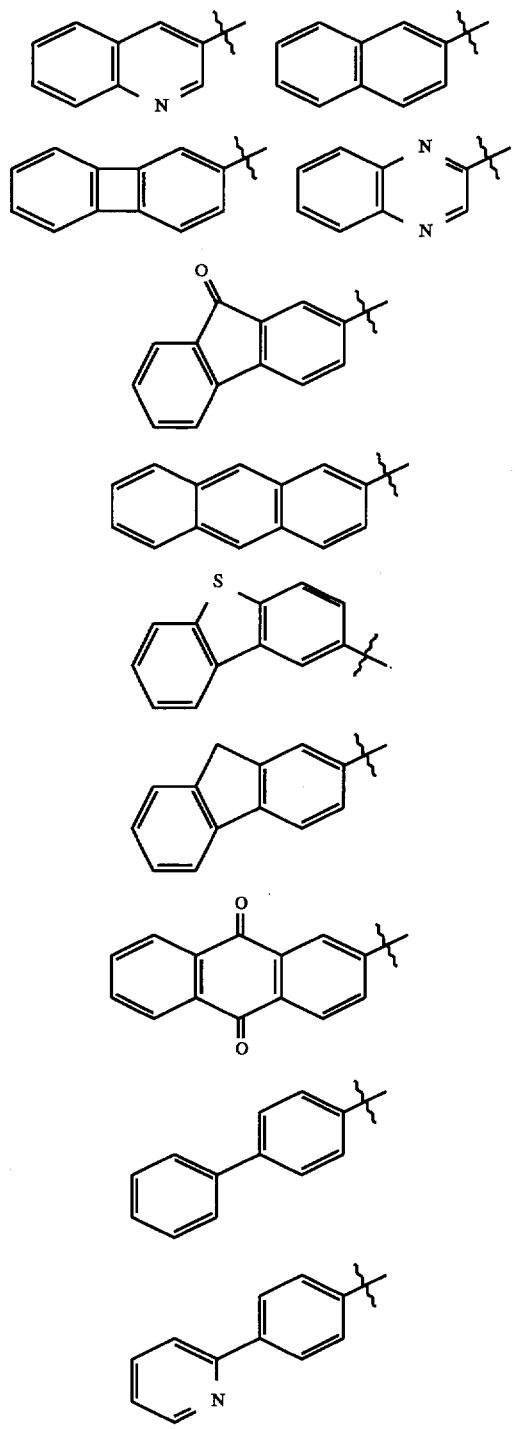

When a compound of the invention is obtained as a mixture of enantiomers, these enantiomers may be separated, when desired, by conventional methods such as crystallization in the presence of a resolving agent, or chromatography, for example using a chiral HPLC column.

Representative compounds of the present invention, which are encompassed by Formula I, include, but are not limited to the compounds in Table 1 and their pharmaceutically acceptable salts. The present invention also encompasses prodrugs, such as acylated prodrugs, of the compounds of Formula I. Those skilled in the art will recognize various synthetic methodologies which may be employed to prepare non-toxic pharmaceutically acceptable addition salts and prodrugs of the compounds encompassed by Formula I.

Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0–4, and the like. Those skilled in the art will recognize a wide variety of non-toxic pharmaceutically acceptable addition salts.

By "alkyl" and "lower alkyl" is meant straight and branched chain alkyl groups having from 1–6 carbon atoms, e.g., $C_1-C_6$ alkyl.

By "lower alkoxy" and "alkoxy" is meant straight and branched chain alkoxy groups having from 1–6 carbon atoms, e.g., $C_1-C_6$ alkoxy.

By halogen is meant fluorine, chlorine, bromine and iodine.

Representative examples of compounds according to the invention are shown in Table 1 below. The number below each compound is its compound number. Each of these compounds may be prepared according to the general reaction Scheme I set forth below.

The invention also pertains to the use of compounds of general Formula I in the treatment of neuropsychological disorders. The pharmaceutical utility of compounds of this invention are indicated by the following assays for dopamine receptor subtype affinity.

ASSAY FOR $D_2$ AND $D_3$ RECEPTOR BINDING ACTIVITY

Pellets of COS cells containing recombinantly produced $D_2$ or $D_3$ receptors from African Green monkey were used for the assays. The sample is homogenized in 100 volumes (w/vol) of 0.05M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 mM spiperone; without further additions, nonspecific binding is less than 20% of total binding. The binding characteristics of representative compounds of the invention for $D_2$ and $D_3$ receptor subtypes are shown in Table 1 for rat striatal homogenates.

TABLE 1

| Compound Number[1] | $D_2$ $K_i$ (nM) | $D_3$ $K_i$ (nM) |
|---|---|---|
| 1 | 127 | 8 |
| 6 | 165 | 17 |
| 7 | 377 | 5 |
| 8 | 250 | 12 |
| 13 | 362 | 10 |
| 14 | 198 | 9 |

[1]Compound numbers correspond to the compounds described below in the examples.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and presenting agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the and partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preparation of Tricyclic Aminoalkylcarboxamides

The compounds of Formula I, and the pharmaceutically acceptable acid addition salts thereof, may be prepared according to the reactions shown below in Scheme 1.

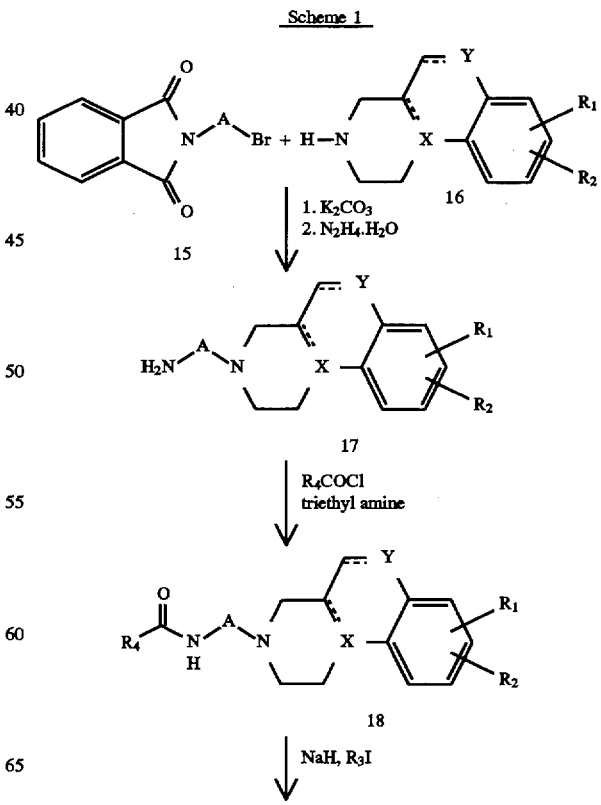

-continued
Scheme 1

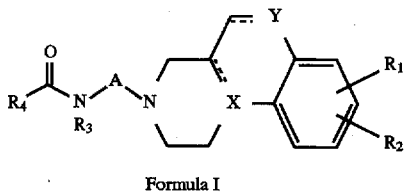

Formula I wherein $R_1$–$R_4$, A, X and Y are as defined above for Formula I.

As shown, an N-aminoalkyl tricyclic amine of structure 17 may be prepared by the condensation of an appropriate tricyclic amine derivative (16) with an N-haloalkylphthalimide. This initial reaction, which is followed by treatment with hydrazine hydrate, may be carried out at room temperature in the presence of a base in a solvent such as acetonitrile. The resulting compound of structure 17 may be condensed in the presence of base with an activated acid derivative, such as an acid chloride ($R_4$COCl) or anhydride to provide secondary carboxamides of structure 18. When it is desirable that $R_3$ be other than hydrogen, i.e, lower alkyl, a compound of formula 18 may be alkylated with an alkyl halide in the presence of base.

Where they are not commercially available, the haloalkylphthalimides may be prepared by literature procedures or procedures analogous to those described in literature. The 1,2,3,4-tetrahydrobenz[f]isoquinolines of general structure 16 used in preparing compounds of Formula IIA can be prepared according to the method of Kessar et at. (Indian J. Chem., 12(2), 113–116, 1974). The 1,2,3,4,5,6-hexahydrobenz[f]isoquinolines of general structure 16 used in preparing compounds of general Formula IIB can be prepared according to the method of Menard et at. (Can. J. Chem., 52, 2316–26, 1974). The bridged 4-phenylpiperazines of general structure 16 used in preparing compounds of general Formula III can be prepared according to the methods of Baxter and Richards (J. Med. Chem., 15, 351–357, 1972), Baxter and Reitz (International Application Publication No. WO 95/11903) or Fried and Potoski (U.S. Pat. No. 4,089,958).

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The disclosures in this application of all articles and references, including patents, are incorporated herein by reference.

The invention is illustrated further by the following examples which are not to be construed as limiting the invention in scope or spirit to the specific procedures described in them. These examples illustrate the presently preferred methods for preparing the compounds of the invention.

EXAMPLE 1

1. 2-(4-aminobutyl)-1,2,3,4-tetrahydrobenz[f]isoquinoline

A solution of 6 g (30.6 mmol) of 1,2,3,4-tetrahydrobenz[f]isoquinoline and 8.70 g (31 mmol) of N-(4-bromobutyl) phthalimide in 100 ml of acetonitrile containing 5 g of potassium carbonate was heated at reflux for 6 h. Upon cooling the reaction mixture was washed with water, dried and concentrated. The resulting material was dissolved in 60 ml of 95% ethanol containing 15 ml of hydrazine hydrate and heated to reflux for 4h. Upon cooling the reaction mixture was concentrated and the resulting solid was stirred for 30 min with diethyl ether, filtered and the filtrate concentrated to provide 7.1 g (86%) of the desired N-aminoalkyl tricyclic amine.

2. N-{4-(1,2,3,4-tetrahydrobenz[f]isoquinolin-2-yl)butyl}-quinoline-3-carboxamide hydrochloride

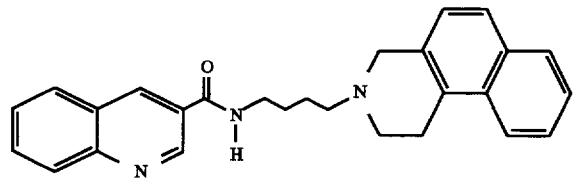

To a solution of 130 mg of 2-(4-aminobutyl)-1,2,3,4-tetrahydrobenz[f]isoquinoline and triethylamine (0.3 ml) in 5 ml of pentene stabilized chloroform was added in one portion to a solution 93 mg of quinoline-3-carbonylchloride in 5 ml of pentene stabilized chloroform. The resulting mixture was washed with 2N NaOH, dried ($Na_2SO_4$) and concentrated. The resulting mixture was purified by chromatography on silica gel eluting with 10% methanol in chloroform to provide the desired product (131 mg, 54%). The hydrochloride salt was prepared in isopropanol.

EXAMPLE 2

The following compounds are prepared essentially according to the procedures set forth above.

(a) N-{4-(1,2,3,4-tetrahydrobenz[f]isoquinolin-2-yl) butyl}-anthracene-2-carboxamide hydrochloride (Compound 2)

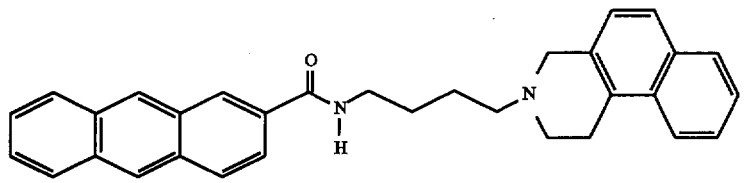

(b) N-{4-(1,2,3,4-tetrahydrobenz[f]isoquinolin-2-yl) butyl}-biphenylene-2-carboxamide hydrochloride (Compound 3)

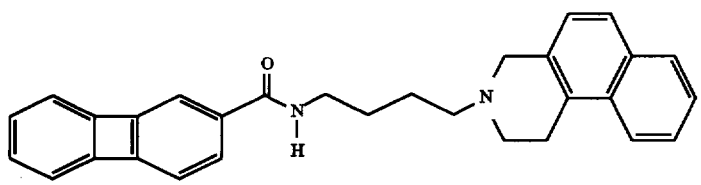

(c) N-{4-(1,2,3,4-tetrahydrobenz[f]isoquinolin-2-yl) butyl}-fluorene-3-carboxamide hydrochloride (Compound 4)

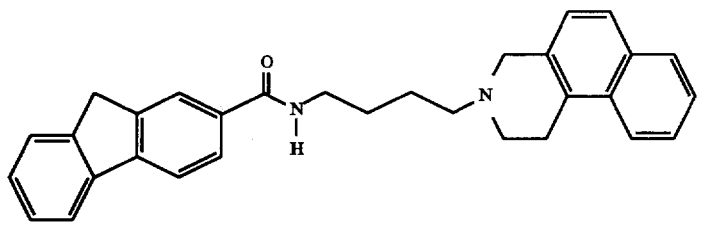

(d) N-{4-(1,2,3,4-tetrahydrobenz[f]isoquinolin-2-yl) butyl}-naphthalene-2-carboxamide hydrochloride (Compound 5)

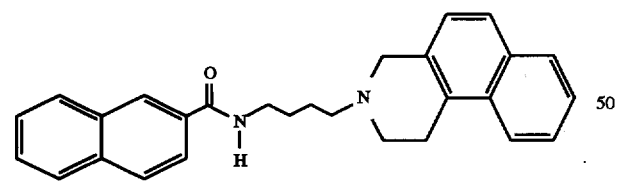

(e) N-{4-(1,2,3,4-tetrahydrobenz[f]isoquinolin-2-yl) butyl}-fluoren-9-one-3-carboxamide hydrochloride (Compound 6)

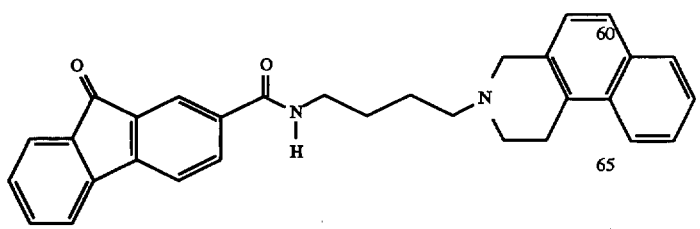

(f) N-{4-(1,2,3,4-tetrahydrobenz[f]isoquinolin-2-yl)butyl}-dibenzothiophene-2-carboxamide hydrochloride (Compound 7)

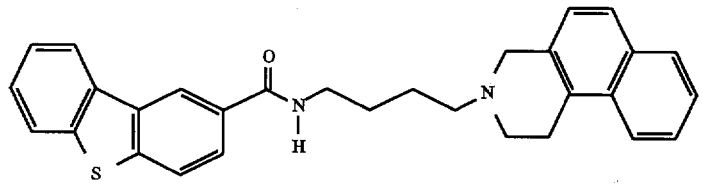

(g) N-{4-(1,2,3,4-tetrahydrobenz[f]isoquinolin-2-yl)butyl}-quinoxaline-2-carboxamide hydrochloride (Compound 8)

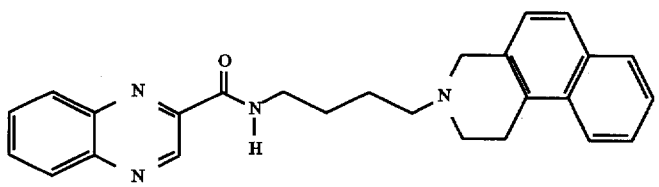

(h) N-{4-(1,2,3,4-tetrahydrobenz[f]isoquinolin-2-yl)butyl}-anthraquinone-2-carboxamide hydrochloride (Compound 9)

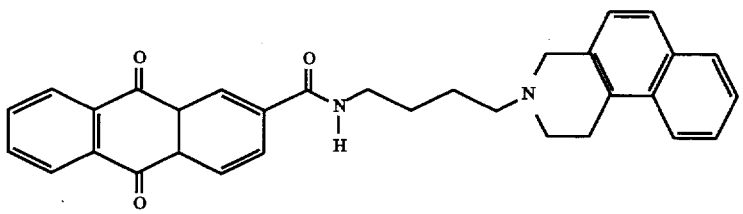

(i) N-{4-(1,2,3,4-tetrahydrobenz[f]isoquinolin-2-yl)butyl}-biphenyl-4-carboxamide hydrochloride (Compound 10)

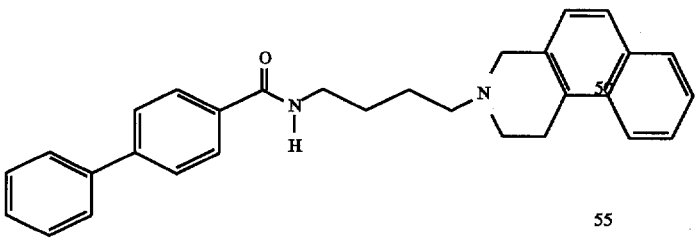

(j) 2-[N-{4-(1,2,3,4-tetrahydrobenz[f]isoquinolin-2-yl)butyl}-4-carboxamidophenyl]pyridine hydrochloride (Compound 11)

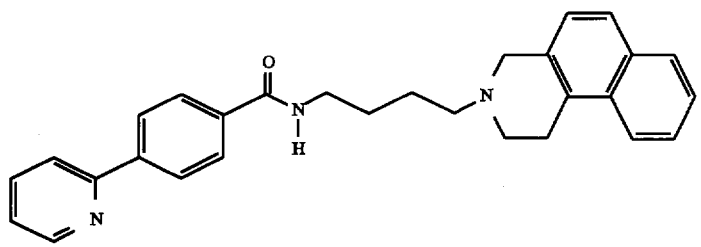

(k) N-{4-(1,2,3,4,4a,5-hexahydropyrazino[2,1-c][1,4]benzoxazin-2-yl)butyl}-fluorene-2-carboxamide hydrochloride (Compound 12)

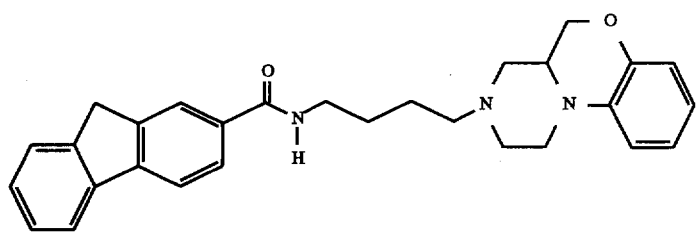

(l) N-{4-(1,2,3,4,5,6-hexahydrobenz[f]isoquinolin-2-yl)butyl}-biphenyl-4-carboxamide hydrochloride (Compound 13)

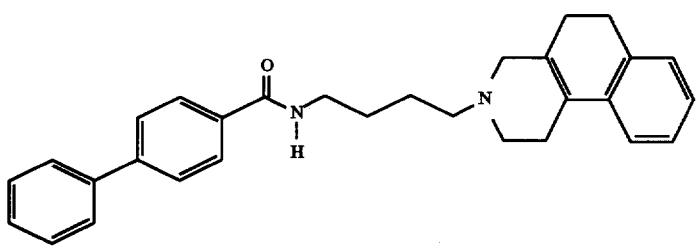

(m) N-{4-(2,3,4,4a,5,6-hexahydro-1H-pyrazino[1,2-a]quinolin-2-yl)butyl}-fluorene-2-carboxamide hydrochloride (Compound 14)

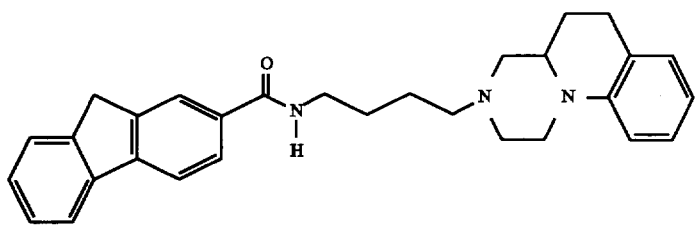

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

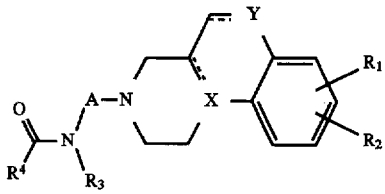

I or the pharmaceutically acceptable acid addition salts thereof wherein:

$R_1$ and $R_2$ are the same or different and represent hydrogen, $C_1-C_6$ alkyl, halogen, hydroxy, amino, cyano, nitro, trifluoromethyl, trifluoromethoxy, $C_1-C_6$ alkoxy, —O$_2$CR', —NHCOR', —COR', —SO$_m$R', where R' is $C_1-C_6$ alkyl and wherein m is 0, 1 or 2; or $R_1$ and $R_2$ independently represent —CONR'R", or —NR'R" where R' and R" independently represent hydrogen or $C_1-C_6$ alkyl;

$R_3$ is hydrogen or lower alkyl;

A represents an alkylene group of 2 to 6 carbon atoms optionally substituted with one or more alkyl groups having from 1 to 4 carbon atoms;

Y represents methylene;

X is C or CH; and $R_4$ is biphenyl, naphthyl, 1 or 2 anthracenyl, 1 or 2 biphenylenyl, dibenzofuranyl, dibenzothiophenenyl, fluorenyl, fluorenonyl, anthroquinonyl, 2-quinoxalinyl or azabiphenyl, each of which is optionally substituted independently by up to three groups selected from halogen, $C_1-C_6$ alkyl, $C_1-C_4$ alkoxy, alkylthio, hydroxy, amino, monoalkylamino, dialkylamino, cyano, nitro, trifluoromethyl or trifluoromethoxy.

2. A compound according to claim 1, which has the formula:

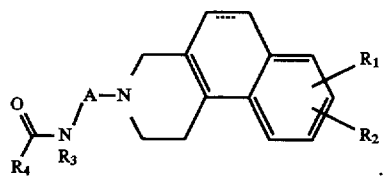

3. A compound according to claim 2, wherein $R_3$ is hydrogen, methyl or ethyl; and A is alkylene of 3–5 carbon atoms.

4. A compound of the formula:

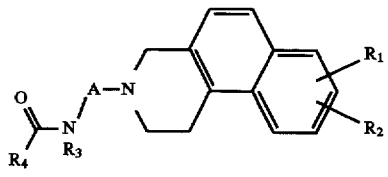

$R^1$ and $R_2$ are the same or different and represent hydrogen, $C_1-C_6$ alkyl, halogen, hydroxy, amino, cyano, nitro, trifluoromethyl, trifluoromethoxy, $C_1-C_6$ alkoxy, —O$_2$CR', —NHCOR', —COR', —SO$_m$R', where R' is $C_1-C_6$ alkyl and wherein m is 0, 1 or 2; or $R_1$ and $R_2$ independently represent —CONR'R", or —NR'R" where R' and R" independently represent hydrogen or $C_1-C_6$ alkyl;

$R_3$ is hydrogen or lower alkyl;

A represents an alkylene group of 2 to 6 carbon atoms optionally substituted with one or more alkyl groups having from 1 to 4 carbon atoms; and $R_4$ is biphenyl, naphthyl, 1 or 2 anthracenyl, 1 or 2 biphenylenyl, dibenzofuranyl, dibenzothiophenenyl, fluorenyl, fluorenonyl, anthroquinonyl, 2-quinoxalinyl or azabiphenyl, each of which is optionally substituted independently by up to three groups selected from halogen, $C_1-C_6$ alkyl, $C_1-C_4$ alkoxy, alkylthio, hydroxy, amino, monoalkylamino, dialkylamino, cyano, nitro, trifluoromethyl or trifluoromethoxy.

5. A compound according to claim 4, wherein $R_3$ is hydrogen and A is alkylene of 3–5 carbon atoms.

6. A compound according to claim 4, wherein A is butylene.

7. A compound according to claim 1, which has the formula

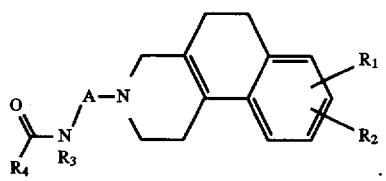

8. A compound according to claim 7, wherein $R_3$ is hydrogen and A is alkylene of 3–5 carbon atoms.

9. A compound according to claim 7, wherein $R_3$ is hydrogen, and A is alkylene of 3–5 carbon atoms.

10. A compound according to claim 9, wherein A is butylene.

11. A compound according to claim 1, which is N-{4-(1,2,3,4-tetrahydrobenz[f]isoquinolin-2-yl)butyl}-quinoline-3-carboxamide.

12. A compound according to claim 1, which is N-{4-(1,2,3,4-tetrahydrobenz[f]isoquinolin-2-yl)butyl}-anthracene-2-carboxamide.

13. A compound according to claim 1, which is N-{4-(1,2,3,4-tetrahydrobenz[f]isoquinolin-2-yl) butyl}-biphenylene-2-carboxamide.

14. A compound according to claim 1, which is N-{4-(1,2,3,4-tetrahydrobenz[f]isoquinolin-2-yl) butyl}-biphenylene-2-carboxamide.

15. A compound according to claim 1, which is N-{4-(1,2,3,4-tetrahydrobenz[f]isoquinolin-2-yl)butyl}-fluorene-3-carboxamide.

16. A compound according to claim 1, which is N-{4-(1,2,3,4-tetrahydrobenz[f]isoquinolin-2-yl)butyl}-naphthalene-2-carboxamide hydrochloride.

17. A compound according to claim 1, which is N-{4-(1,2,3,4-tetrahydrobenz[f]isoquinolin-2-yl)butyl}-fluoren-9-one-3-carboxamide hydrochloride.

18. A compound according to claim 1, which is N-{4-(1,2,3,4-tetrahydrobenz[f]isoquinolin-2-yl)butyl}-dibenzothiophene-2-carboxamide hydrochloride.

19. A compound according to claim 1, which is N-{4-(1,2,3,4-tetrahydrobenz[f]isoquinolin-2-yl)butyl}-quinoxaline-2-carboxamide hydrochloride.

20. A compound according to claim 1, which is N-{4-(1,2,3,4-tetrahydrobenz[f]isoquinolin-2-yl)butyl}-anthraquinone-2-carboxamide hydrochloride.

21. A compound according to claim 1, which is N-{4-(1,2,3,4-tetrahydrobenz[f]isoquinolin-2-yl)butyl}-biphenyl-4-carboxamide hydrochloride.

22. A compound according to claim 1, which is 2-[N-{4-(1,2,3,4-tetrahydrobenz[f]isoquinolin-2-yl)butyl}-4-carboxamidophenyl]pyridine hydrochloride.

23. A compound according to claim 1, which is N-{4-(1,2,3,4,5,6-hexahydrobenz[f]isoquinolin-2-yl)butyl}-biphenyl-4-carboxamide hydrochloride.

* * * * *